United States Patent
Fischvogt

(10) Patent No.: US 7,938,804 B2
(45) Date of Patent: May 10, 2011

(54) SURGICAL ACCESS APPARATUS WITH SEAL AND CLOSURE VALVE ASSEMBLY

(75) Inventor: Gregory Fischvogt, Hamden, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/710,499

(22) Filed: Feb. 23, 2010

(65) Prior Publication Data

US 2010/0249711 A1    Sep. 30, 2010

Related U.S. Application Data

(60) Provisional application No. 61/164,597, filed on Mar. 30, 2009.

(51) Int. Cl.
*A61M 5/178* (2006.01)

(52) U.S. Cl. ......... 604/167.03; 604/167.01; 604/167.06; 606/108

(58) Field of Classification Search ............. 604/164.01, 604/164.04, 164.12, 165.04, 158, 264, 167.01, 604/167.02, 167.03, 167.04, 167.06, 256; 606/108

See application file for complete search history.

(56) References Cited

U.S. PATENT DOCUMENTS

| | | | |
|---|---|---|---|
| 4,655,752 A * | 4/1987 | Honkanen et al. | 604/256 |
| 4,960,412 A * | 10/1990 | Fink | 604/167.04 |
| 5,154,701 A * | 10/1992 | Cheer et al. | 604/167.03 |
| 5,180,373 A * | 1/1993 | Green et al. | 604/167.03 |
| 5,613,954 A | 3/1997 | Nelson et al. | |
| 5,957,888 A * | 9/1999 | Hinchliffe | 604/117 |
| RE36,702 E * | 5/2000 | Green et al. | 606/167 |
| 7,037,344 B2 | 5/2006 | Kagan et al. | |
| 7,083,626 B2 * | 8/2006 | Hart et al. | 606/108 |
| 7,632,250 B2 * | 12/2009 | Smith et al. | 604/167.06 |
| 2004/0066008 A1 * | 4/2004 | Smith | 277/628 |
| 2008/0149685 A1 | 6/2008 | Smith et al. | |
| 2008/0171987 A1 * | 7/2008 | Franer et al. | 604/167.03 |
| 2008/0249475 A1 * | 10/2008 | Albrecht et al. | 604/167.06 |
| 2009/0082720 A1 * | 3/2009 | Smith | 604/30 |
| 2009/0093752 A1 | 4/2009 | Richard et al. | |

(Continued)

FOREIGN PATENT DOCUMENTS

EP    1 709 918    10/2006

(Continued)

OTHER PUBLICATIONS

European Search Report for EP 10 25 0629 date of completion is Jun. 28, 2010 (3 pages).

*Primary Examiner* — Nicholas D Lucchesi
*Assistant Examiner* — Quynh-Nhu H Vu

(57) ABSTRACT

A surgical access apparatus includes an access housing, an access member extending from the access housing, a seal mount disposed within the access housing and having an object seal for forming a seal about the surgical object and a monolithic closure valve mounted to the housing distal of the seal mount. The access housing and the access member define a longitudinal passage for passage of a surgical object. The closure valve includes an interface segment and a closure segment extending from the interface segment. The interface segment is in contacting relation with the seal mount and comprises a generally compilable material adapted to maintain a substantial seal with the seal mount and within the longitudinal passageway during angular movement of the surgical object.

10 Claims, 8 Drawing Sheets

U.S. PATENT DOCUMENTS

2010/0100043 A1 4/2010 Racenet

FOREIGN PATENT DOCUMENTS

| | | |
|---|---|---|
| EP | 2 042 114 | 4/2009 |
| EP | 2 044 889 | 4/2009 |
| EP | 2 087 846 | 8/2009 |
| WO | 2005/018426 | 3/2005 |
| WO | 2007/121747 | 11/2007 |
| WO | WO 2008/045744 | 4/2008 |
| WO | WO 2008/093313 | 8/2008 |

* cited by examiner

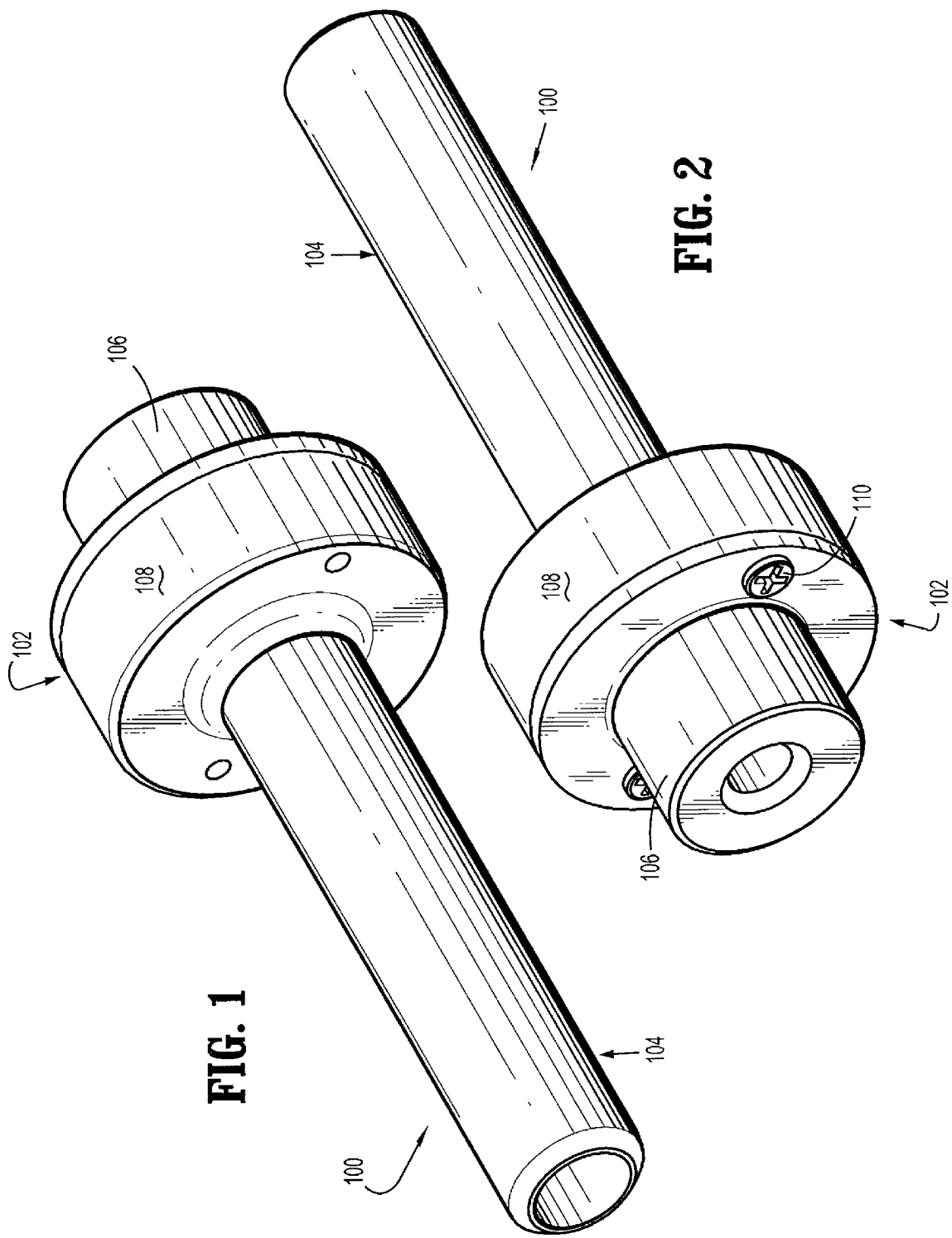

SURGICAL ACCESS APPARATUS WITH SEAL AND CLOSURE VALVE ASSEMBLY

CROSS REFERENCE TO RELATED APPLICATION

The present application claims the benefit of and priority to U.S. Provisional Application Ser. No. 61/164,597 filed on Mar. 30, 2009, the entire contents of which are incorporated herein by reference.

BACKGROUND

1. Technical Field

The present disclosure relates to a surgical access apparatus for accessing an underlying body cavity to permit the introduction of a surgical object into the cavity. In particular, the present disclosure relates to an access apparatus including a seal and closure valve assembly adapted to receive the surgical object in sealed engagement while maintaining the seal about the object and within the passageway of the access apparatus during manipulation of the surgical object.

2. Description of the Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere. In view of the need to maintain the atmospheric integrity of the inner area of the cavity, a seal assembly for a cannula, which permits introduction of a wide range of surgical instrumentation and maintains the atmospheric integrity of the inner area of the cavity is desirable. In this regard, there have been a number of attempts in the prior art to achieve such sealing requirements. A difficulty encountered with conventional seal assemblies, however, is the inability of accommodating the wide range of sizes of instrumentation. In addition, angulation (i.e., angular movement) and/or manipulation of instrumentation within the cannula often present difficulties with respect to maintaining seal integrity both about the instrumentation and within the passageway of the cannula.

SUMMARY

Accordingly, the present disclosure is directed to a surgical access apparatus including an access housing, an access member extending from the access housing, a seal mount disposed within the access housing and having an object seal for forming a seal about the surgical object and a monolithic closure valve mounted to the housing distal of the seal mount. The access housing and the access member define a longitudinal passage for passage of a surgical object. The closure valve includes an interface segment and a closure segment extending from the interface segment. The interface segment is in contacting relation with the seal mount and comprises a generally compilable material adapted to maintain a substantial seal with the seal mount and within the longitudinal passageway during angular movement of the surgical object.

In another embodiment, a surgical access apparatus includes an access housing, an access member extending from the access housing, an object seal mount disposed within the access housing and having an object seal for forming a seal about the surgical object and a closure valve mounted to the housing distal of the object seal mount. The access housing and the access member have a longitudinal passage for passage of a surgical object. The object seal mount is adapted for at least one of angular movement and rotational movement relative to the longitudinal axis upon manipulation of the surgical object. The closure valve includes an interface segment and a closure segment extending from the interface segment. The interface segment is in contacting relation with the object seal mount and comprises a generally compilable material adapted to maintain a substantial seal with the object seal mount and within the longitudinal passageway during angular movement of the object seal mount.

The closure segment may be adapted to substantially close in the absence of the surgical object. The closure valve may be monolithically formed. The interface segment may define an aperture for at least partially accommodating the object seal mount. The interface segment may define a sloped interfacing surface adjacent the aperture. The sloped interfacing surface may be dimensioned to contact the object seal mount and facilitate angular movement thereof while maintaining the substantial seal with the object seal mount and the closure valve.

The object seal mount may be a substantially hemispherical member having a curved outer mount surface and the interface segment of the closure valve may define a curved interfacing surface generally corresponding to the curved outer mount surface. The respective surfaces cooperate to permit angular or rotational movement of the object seal mount relative to the closure valve while establishing and maintaining a substantial sealed relation between the components.

The access housing may include an inner wall and an outer wall. The object seal mount may be at least partially accommodated within an annular space defined between the inner and outer walls. The inner wall includes curved surfaces adjacent the object seal mount. The curved surfaces cooperate with a curved inner mount surface of the object seal mount during angular movement thereof. The interface segment is adapted to be biased against the object seal mount in response to a pressurized environment present in the longitudinal passageway.

The present disclosure provides an access apparatus and associated seal and closure valve assembly with a reduced number of components, while increasing the effectiveness of the seal assembly during angulation of a surgical instrument and also reducing the cost of the assembly.

BRIEF DESCRIPTION OF THE DRAWINGS

The foregoing features of the present disclosure will become more readily apparent and will be better understood by referring to the following detailed description of particular embodiments, which are described hereinbelow with reference to the drawings wherein:

FIGS. 1-2 are perspective views of a surgical access apparatus in accordance with the principles of the present disclosure;

DETAILED DESCRIPTION

Figure 3:
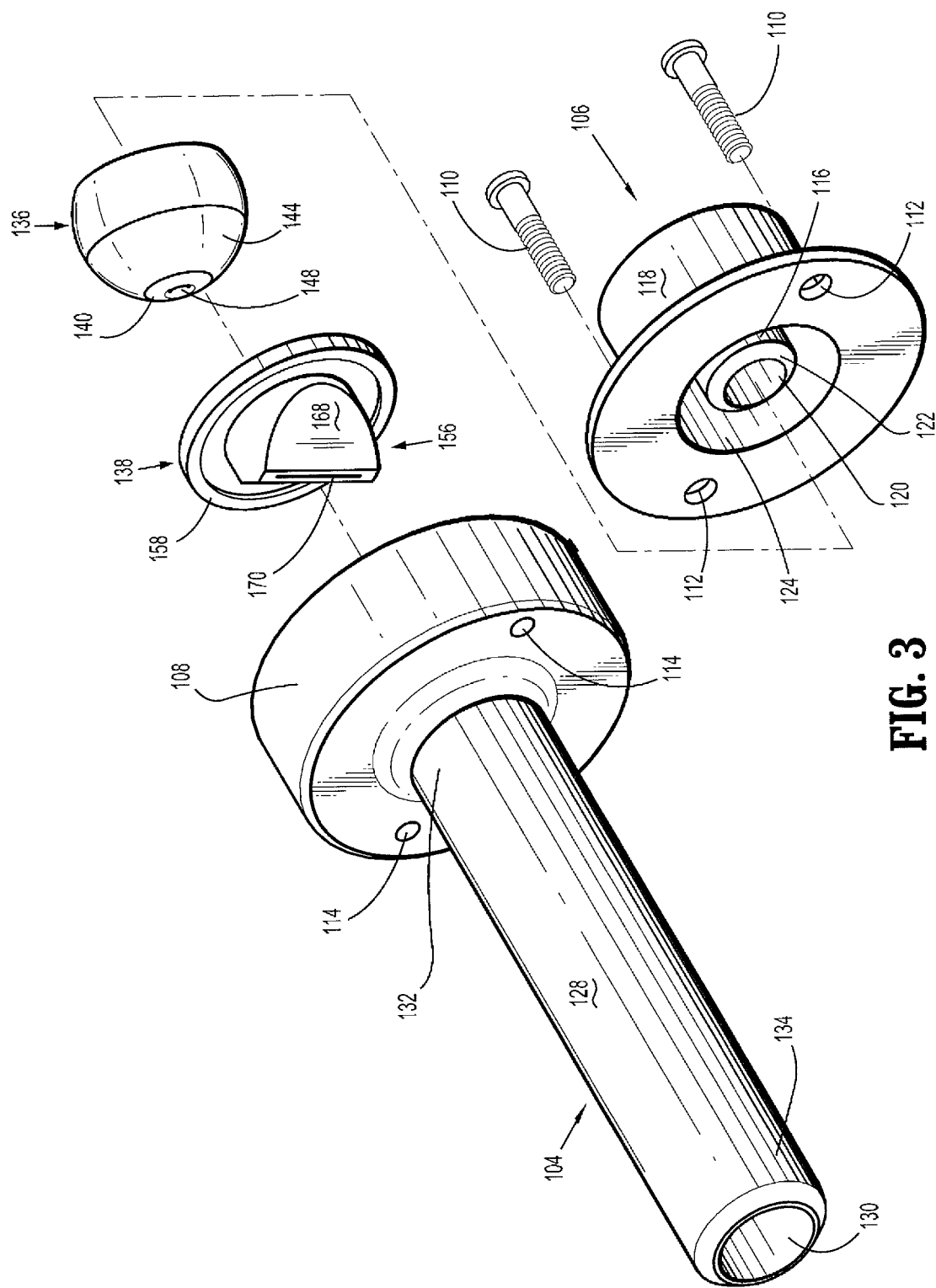
FIG. 3 is a perspective view with parts separated of the access apparatus illustrating the access housing, access member, object seal mount and closure valve.

The present disclosure relates to an access apparatus including an object seal mount and closure valve assembly having a reduced number of components as compared to the prior art, thereby increasing the effectiveness of the assembly during angulation of a surgical instrument while also reducing the cost of the assembly. The object seal mount and closure valve assembly may include a seal that is capable of movement while maintaining contact with an interface segment or seal of the closure valve thereby maintaining the integrity of the seal within the passageway of the apparatus.

The access apparatus permits the introduction and manipulation of various types of surgical objects including instrumentation adapted for insertion while maintaining a fluid tight interface about the instrumentation to preserve the atmospheric integrity of a surgical procedure from gas and/or fluid leakage. Specifically, the assembly accommodates angular manipulation of the surgical instrument. This feature of the present disclosure desirably minimizes the entry and exit of gases and/or fluids to/from the body cavity.

Access apparatus may be any suitable cannula assembly used in laparoscopic or arthroscopic procedures. Access apparatus may also be adapted to receive the hand of a surgeon during, e.g., a minimally invasive laparoscopic hand assisted procedure.

Examples of objects or instrumentation include the surgeon's hand, clip appliers, graspers, dissectors, retractors, staplers, laser probes, photographic devices, endoscopes and laparoscopes, tubes, and the like. Such instruments will be collectively referred to herein as "instruments or instrumentation".

In the following description, as is traditional, the term "proximal" or "trailing" refers to the portion of the instrument closest to the operator while the term "distal" or "leading" refers to the portion of the instrument remote from the operator.

Referring now to the drawings, in which like reference numerals identify identical or substantially similar parts throughout the several views, FIGS. 1-2 illustrate an exemplary embodiment of the access apparatus 100 in accordance with the principles of the present disclosure. Access apparatus 100 may be a laparoscopic cannula assembly utilized in conjunction with a laparoscopic surgical procedure where the peritoneal cavity is insufflated with a suitable gas, e.g., $CO_2$, to raise the cavity wall from the internal organs therein. The cannula assembly may be used with an obturator assembly (not shown) which is a sharp pointed instrument (e.g., sharp and/or pointed, bladeless, or any other suitable shape) positionable within the passageway of the cannula assembly. The obturator assembly is utilized to penetrate the abdominal wall and then subsequently removed from the cannula assembly to permit introduction of the surgical instrumentation utilized to perform the procedure. In the alternative, access apparatus 100 may be an arthroscopic cannula assembly used in connection with an arthroscopic surgical procedure.

Figure 4:
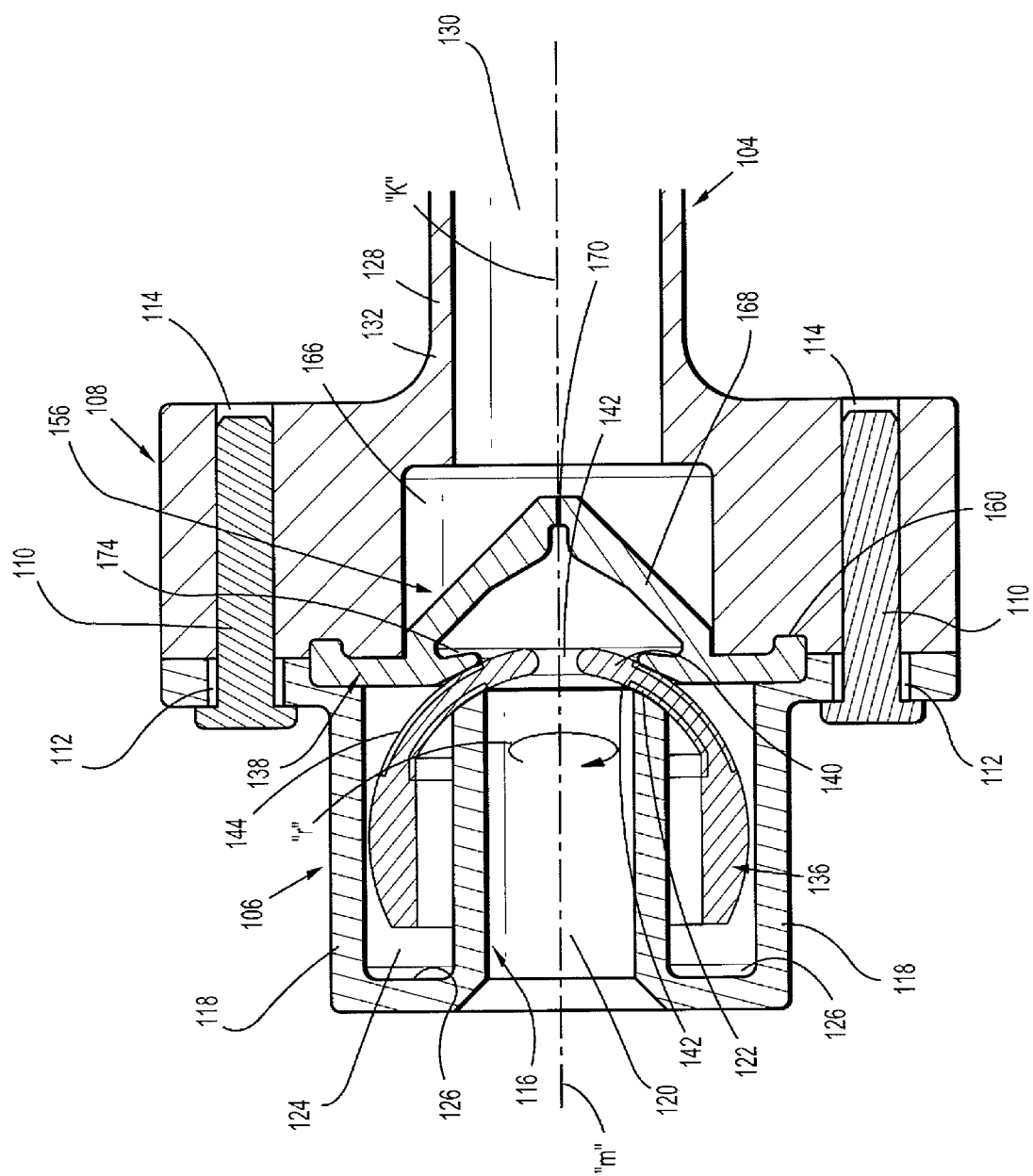
FIG. 4 is a cross-sectional view of the access housing illustrating the object seal mount and closure valve mounted within the access housing.
Figure 5A:
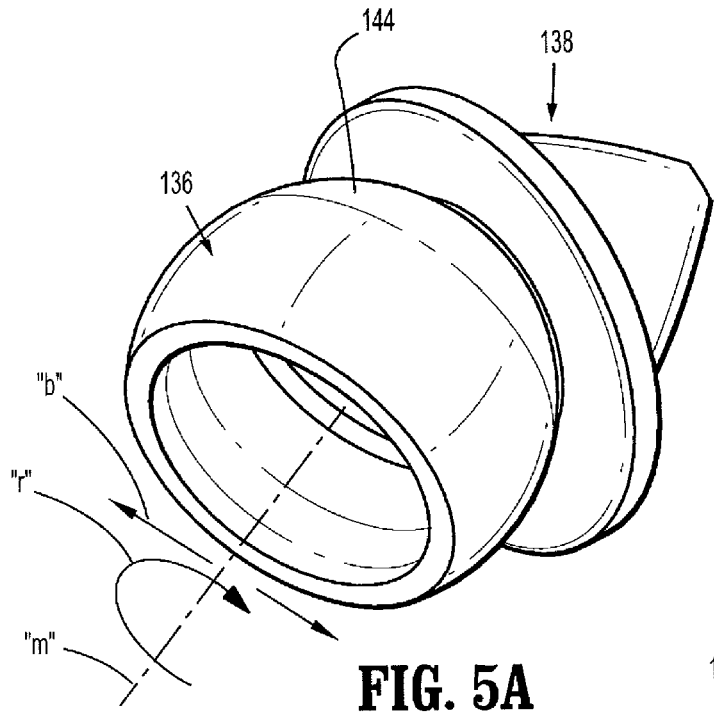
FIG. 5A is a perspective view of the object seal mount and closure valve of the access apparatus.
Figure 5B:
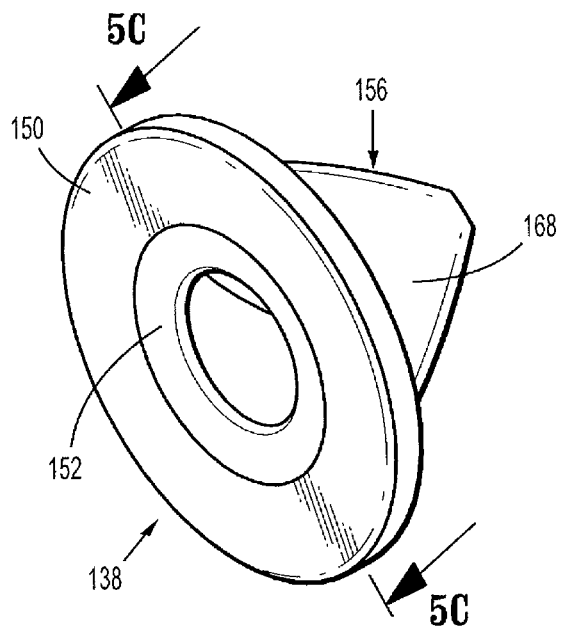
FIG. 5B is a perspective view of the closure valve.
Figure 5C:
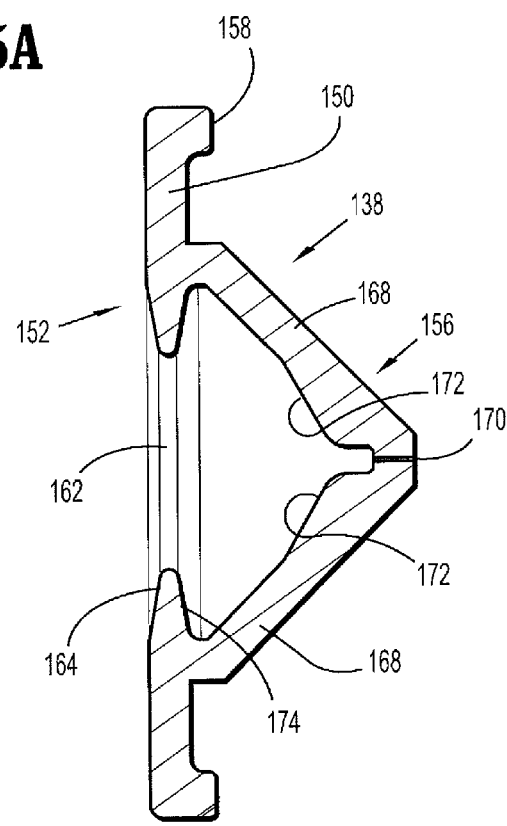
FIG. 5C is a cross-sectional view of the closure valve taken along the lines 5C-5C of FIG. 5B.

With reference to FIGS. 3-4, in conjunction with FIGS. 1-2, access apparatus 100 includes access housing 102 and elongated access member 104 extending from the access housing 102. Access housing 100 may include multiple housing segments, namely, first housing segment 106 and second housing segment 108, connected to each other via convention means. In one embodiment, first and second housing segments 106, 108 are connected with the use of mounting screws 110 extending through apertures 112 of first housing segment 106 and threaded apertures 114 of second housing segment 108 to connect the components. Other means for connecting first and second housing segments 106, 108 are also envisioned including with the use of adhesives, cements, welding or the like. In the alternative, first and second housing segments 106, 108 may be a single component integrally or monolithically formed.

Referring still to FIGS. 1-4, first housing segment 106 includes annular or cylindrical inner guide wall 116 and outer wall 118 disposed radially outwardly of the inner guide wall 116. Inner guide wall 116 defines central passage 120 which is dimensioned to receive a surgical object or instrument (not shown) and laterally confine the instrument within access housing 102. Inner guide wall 116 is generally cylindrical in configuration and terminates in a distal arcuate surface 122. Inner guide wall 116 and outer wall 118 define annular space 124 therebetween terminating in internal bearing surfaces 126.

Access member 104 may be a sleeve member defining a longitudinal axis "k" extending along the length of the access member. Access member 104 includes outer sleeve wall 128 defining an internal longitudinal passage 130 extending from proximal or trailing end 132 through distal or leading end 134 of the access member 104. Longitudinal passage 130 of access member 104 is in general longitudinal alignment with central passage 120 of access housing 102 to define a common longitudinal passageway 120, 130 through access apparatus 100 for passage of the surgical object. Access member 102 may be a separate component connected to second housing segment 108 or may be monolithically formed with the second housing segment 108 as shown. Access member 104 may be formed of stainless steel or other rigid materials such as a polymeric material or the like. Access member 104 may be clear or opaque. The diameter of access member 104 may vary, but typically ranges from about 3 to about 15 mm when used in a laparoscopic or arthroscopic technique. If used in a hand assisted minimally invasive approach, the diameter of access member may be substantially greater than 15 mm.

Referring now to FIGS. 3-6, access apparatus 100 further includes object seal mount 136 and closure valve 138 each being at least partially disposed within access housing 102. Object seal mount 136 includes an object seal 140 adapted to form a seal about the surgical object. Object seal mount 136 may be substantially planar or may be generally spherical or hemispherical in shape as shown. The materials of fabrication of object seal mount 136 may include an elastomeric material, a polymeric material and/or combinations thereof.

Figure 6:
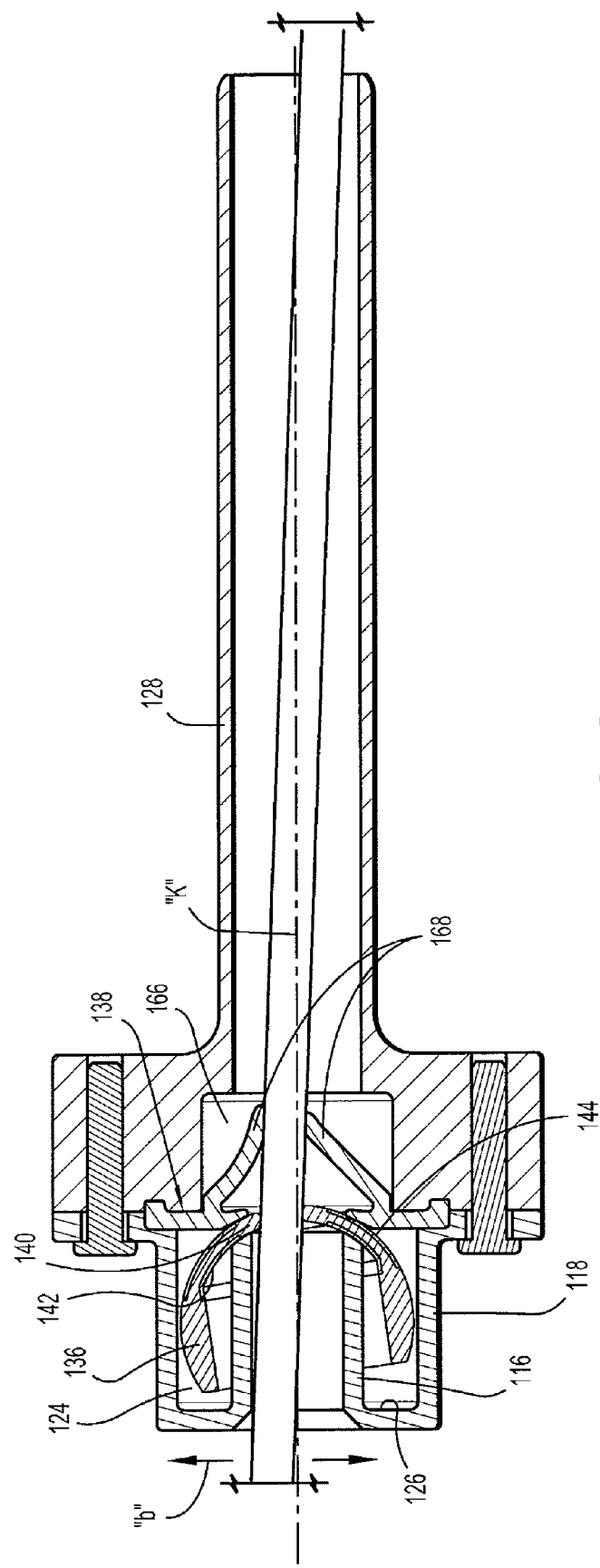
FIG. 6 is a cross-sectional view of the access apparatus illustrating a surgical object positioned therein.

Object seal mount 136 is at least partially received within annular space 124 defined between inner guide wall 116 and outer wall 118, and may be mounted in a manner which permits angulation, i.e., angular movement, of the object seal mount 136 relative to longitudinal axis "k". Specifically, object seal mount 136 is capable of rotational movement "r" about an axis of rotation "m" which may be coincident with longitudinal axis "k". In addition, object seal mount 136 may pivot or angulate relative to longitudinal axis "k" in the direction of directional arrows "b" in response to angular movement of a surgical instrument "i" (FIG. 6). During pivotal movement, object seal mount 136 traverses annular space 124 defined between inner guide wall 116 and outer wall 118 of access housing 102. The range of pivoting or angulating movement of object seal mount 130 may be limited by internal bearing surfaces 126 adjacent annular space 124. This compound range of movement enables the surgeon to manipulate the surgical instrument "I" or object in many directions thus enhancing access to underlying tissue sites and facilitating performance of the surgical procedure.

As best depicted in FIGS. 5-6, object seal mount 136 and object seal 140 include inner mount surface 142 and outer mount surface 144. Inner mount surface 142 defines an arcuate profile generally corresponding to distal arcuate surface 122 of inner guide wall 116 of first housing segment 106 (FIGS. 3 and 4). During manipulation of object seal mount 136 relative to access housing 102, inner mount surface 142 traverses (including pivotal and rotational movement) arcuate surface 122 of inner guide wall 116 of first housing segment 106. Inner mount surface 142 and/or arcuate surface 122 of first housing segment 106 may include a lubricious coating to facilitate movement of object seal mount 130.

Object seal 140 may be a separate component and secured to the object seal mount 136 via conventional means. In the alternative, object seal 140 may be monolithically formed with object seal mount 136. Object seal 140 may define a passage 148 such as a slit, aperture or the like to permit passage of the surgical object in substantial sealed relation therewith. The materials of fabrication of object seal 148 may include a suitable elastomeric material whereby the inner portions defining passage 148, conform to establish the seal about the surgical object. One suitable seal which may be adapted for incorporation within object seal mount 136 is disclosed in commonly assigned U.S. Pat. No. 6,482,181 to Racenet et al., the entire contents of which are hereby incorporated by reference herein. The seal disclosed in the Racenet '181 patent includes an elastomeric material (such as isoprene or natural rubber) and at least one layer of fabric material. The fabric material may be any suitable fabric, for example, A SPANDEX material containing about 20% LYCRA and about 80% NYLON available from Milliken. The elastomeric material may be adhered to or embedded within the fabric material.

As best depicted in FIGS. 4 and 5A-5C, closure valve 138 includes circumferential skirt or flange 150, interface segment 152 depending radially inwardly from the flange 150 and closure segment 156. Circumferential flange 150 is secured between first and second housing segments 106, 108 when the first housing segment 106 is assembled with the second housing segment 108. In one embodiment, circumferential flange 150 includes an outermost annular rib 158 which is received within a correspondingly dimensioned recess 160 of second housing segment 108 (FIG. 4). Annular rib 158 and annular recess 160 cooperate to confine circumferential flange 150 within first and second housing segments 106, 108.

Interface segment 152 defines central aperture 162 for at least partial reception of object seal mount 136 and/or object seal 140. Interface segment 152 is adapted to establish and maintain a substantial seal with object seal mount 136. In particular, interface segment 152 has trailing or proximal interfacing surface 164 which contacts object seal mount 136, i.e., outer mount surface 144 of the object seal mount 136, when the unit is assembled. Interfacing surface 164 interfaces with outer mount surface 144 of object seal mount 136 during rotating and/or angulation of object seal mount 136. In one embodiment, interfacing surface 164 defines a tapered or sloped arrangement cooperating with the outer contour of outer mount surface 144 to create an area of contact between the two components. Interface segment 152 is formed of a generally pliable or conformable or compliant material to deflect and/or accommodate object seal mount 136 during movement within access housing 102. Interface segment 152 and outer mount surface 144 of object seal mount 136 establish and maintain a substantial sealed relation between the interface segment 152 and object seal mount 136 thereby substantially minimizing passage of gases about the object seal mount 136 and through longitudinal passageway 120, 130 of access apparatus 100. A suitable lubricious coating may be applied to interfacing surface 164 and/or outer mount surface 144 of object seal mount 136 to facilitate movement of the object seal mount 136 relative to closure valve 138. Suitable materials of fabrication for interface segment 152 include elastomers such as isoprene, natural rubber or the like. Interface segment 152 may deflect in either or both an axial or radial direction relative to longitudinal axis "k" during manipulation of the surgical object and movement of object seal mount 136.

Closure segment 156 of closure valve 138 extends radially inwardly and longitudinally with respect to longitudinal axis "k and is at least partially accommodated within an internal volume 166 of second housing segment 108. Closure segment 156 may function as a zero closure valve that is adapted to substantially close in the absence of the surgical object. In one embodiment, closure segment 156 includes first and second flaps 168 tapering inwardly to slit 170. Flaps 168 are normally biased to the closed position and open upon insertion of the surgical object. Flaps 168 also may close in response to the presence of a pressurized environment within access member 104 during, e.g., a laparoscopic surgical procedure. Ribs 172 may extend along an inner surface of closure segment 156 positioned adjacent slit 170 to engage the surgical object upon introduction within access housing 102. Ribs 172 may enhance the structural integrity of closure segment 156. Closure segment 156 may define a general duckbill shape. In the alternative, closure segment 156 may define a trumpet shape. As a further alternative, closure segment 156 may include multiple slit arrangements. Materials of fabrication of closure segment 156 may include isoprene or natural rubber or any other suitable elastomeric material.

In one embodiment, closure valve 138 including circumferential flange 150, interface segment 152 and closure segment 156, are monolithically formed as a single unit. This enhances assembly of the apparatus and improves the overall sealing capacity of access apparatus 100. Any elastomeric material including isoprene, natural rubber, foam, gel or the like may be suitable as the material of fabrication of closure valve 138.

A method of assembly of access apparatus 100 now will be discussed. With reference to FIGS. 3-5C, closure valve 138 is positioned within second housing segment 108 of access housing 102 with annular rib 158 received within annular recess 160 of the second housing segment 108. A lubricant may be applied to interfacing surface 164 of interface segment 152. Object seal mount 136 is then placed in interfacing and contacting relationship with interfacing surface 164 of interface segment 152 with at least a portion of object seal mount 136 and object seal 138 residing within central aperture 162 of the interface segment 152. The distal arcuate surface 122 of inner guide wall 116 of first housing segment 106 may be lubricated with an appropriate coating. Similarly, inner mount surface 142 of object seal mount 136 and object seal 140 may be coated with a lubricant. First housing segment 106 is then mounted over object seal mount 136. Mounting screws 110 are introduced within apertures 112 of first housing segment 106 and secured with threaded apertures 114 of second housing segment 108.

Figure 7:
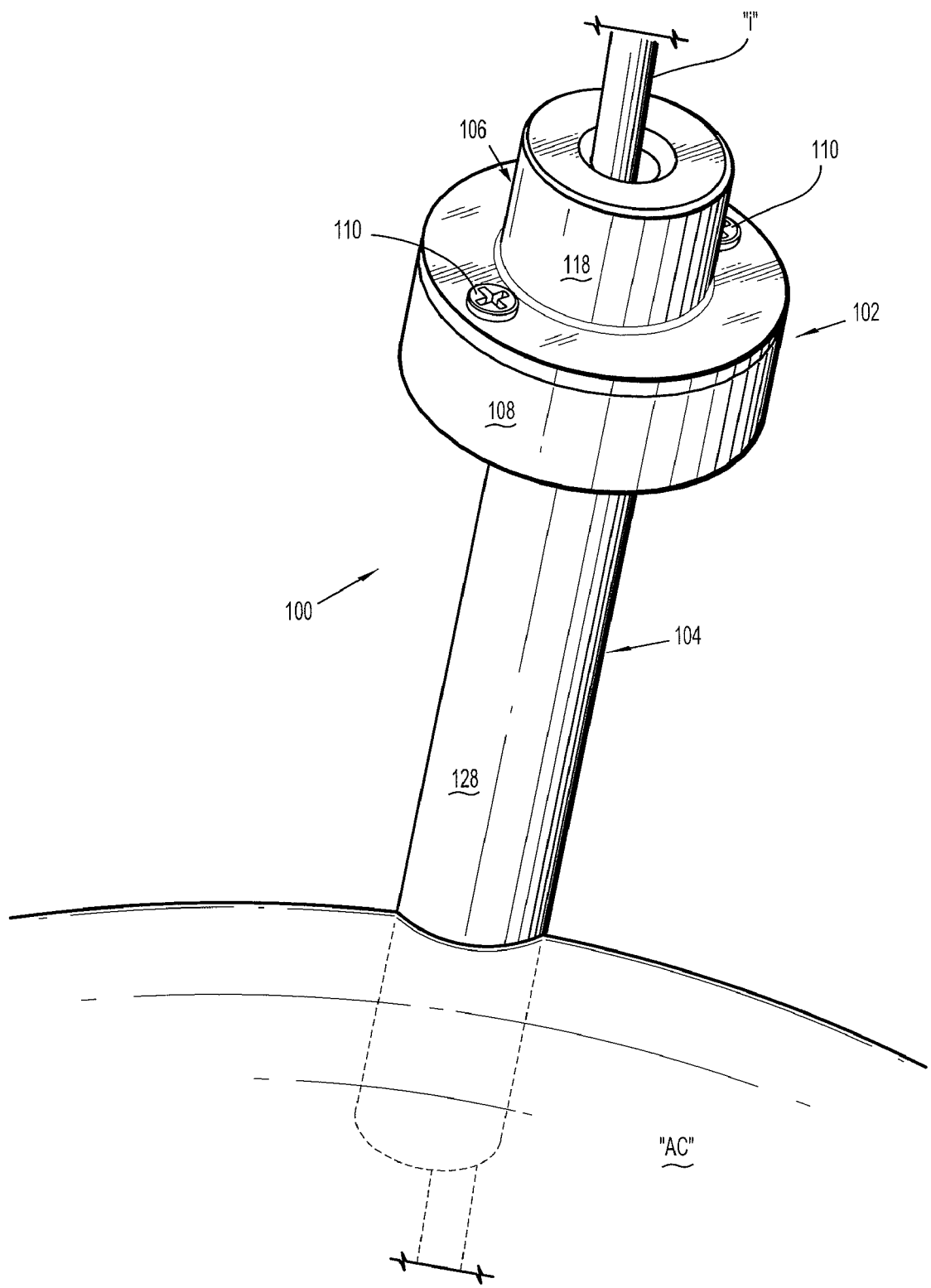
FIG. 7 is a view illustrating the access apparatus accessing an internal cavity of a patient with a surgical object.

Referring now to FIG. 7, the use of access apparatus 100 will be discussed. Access apparatus 100 is introduced within body tissue to access an underlying body cavity "AC", e.g., an insufflated body cavity such as the peritoneal cavity, with the use of, e.g., an obturator. With access member 104 extending through the peritoneal lining, a surgical object or instrument "i" may be advanced through longitudinal passageway 120, 130 defined by access housing 102 and access member 104. If the axis of the instrument "i" is not aligned with passage 148 of object seal 140, the surgical instrument "i" will contact the inner guide wall 116 and/or inner mount surface 142 of object seal mount 136. In either event, object seal mount 136 will swivel (rotate and/or pivot) to align the surgical instrument "i" with passage 148 of object seal 140. Passage 148 stretches to accommodate the diameter of the instrument "i", as necessary. The instrument "i" passes further distally into the second housing segment 108 passing through closure valve 138, access member 104 and into the body cavity "AC". The instrument "i" may be maneuvered relative to access housing 102 and the longitudinal axis "k" to perform various tasks inherent in the surgical procedure. During this movement, object seal mount 136 may also correspondingly pivot and/or rotate relative to closure valve 138 and longitudinal axis "k" while interfacing surface 164 of interface segment 152 and outer mount surface 144 of object seal mount 136 maintain their substantial sealed relationship to thereby substantially minimize passage of gases about object seal mount 136 and through access housing 102 and to the environment.

In addition, the insufflation gases and corresponding pressurized environment within access member 104 provides steady pressure on the leading or distal surface 174 of interface segment 164 when the closure segment 156 is open, e.g., when the surgical instrument is extending through access member 104. This upward pressure or force biases interface segment 152 and interfacing surface 164 against outer mount surface 144 of object seal mount 136 and possibly against object seal 140. The force may be transferred to object seal mount 136 allowing the object seal mount 136 and object seal 140 to locate itself on the distal arcuate surface 122 of the first housing segment 106 of access housing 102. It is the upward pressure in combination with slight compression between object seal mount 136, e.g., outer mount surface 144 and/or object seal 140 which creates an airtight seal between the surfaces of object seal mount 136 and closure valve 138.

Figure 8:
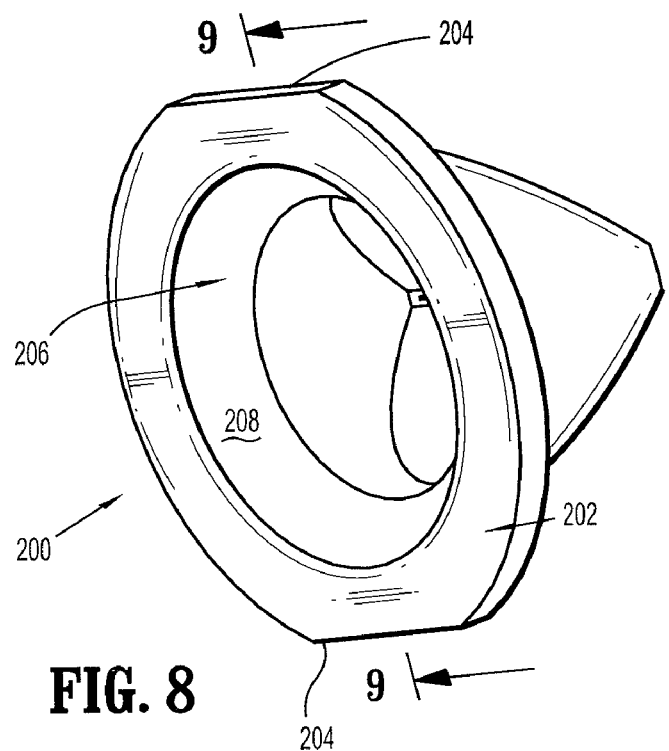
FIG. 8 is a perspective view of an alternate embodiment of a closure valve.
Figure 9:
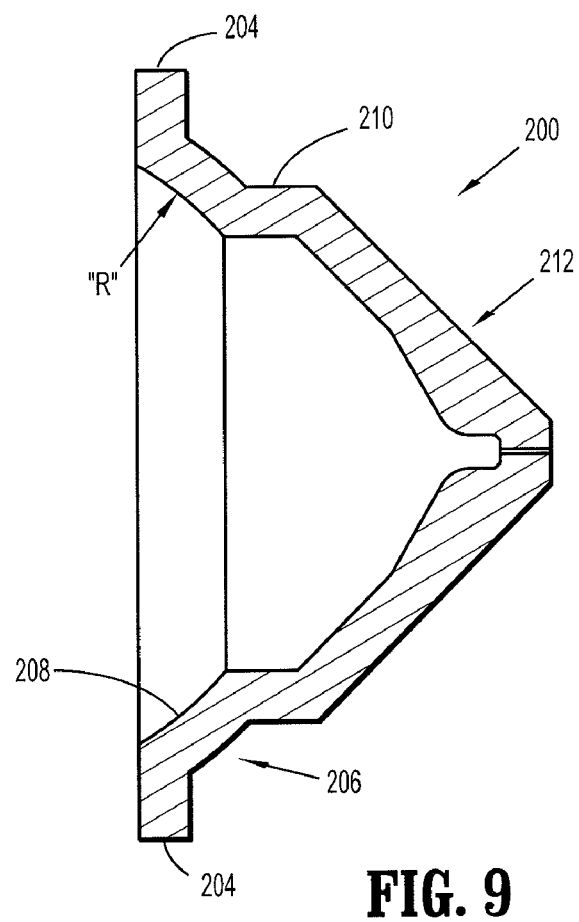
FIG. 9 is a cross-sectional view of the closure valve of FIG. 8 taken along the lines 9-9 of FIG. 8.
Figure 10:
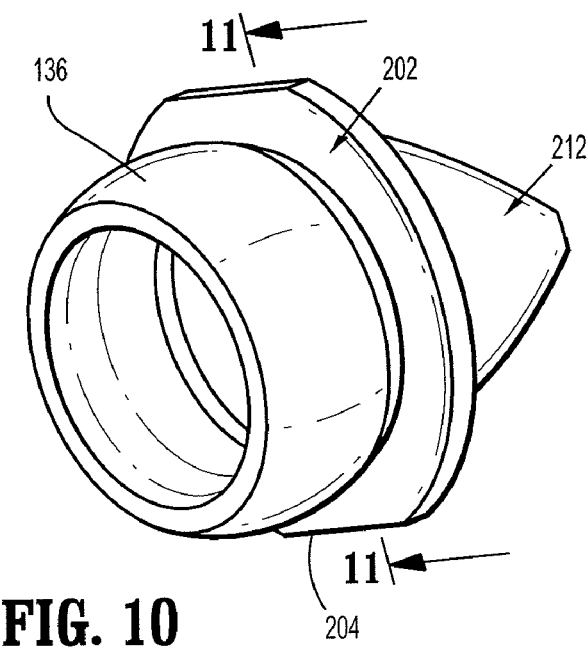
FIG. 10 is a perspective view of the object seal mount and the closure valve of FIGS. 8 and 9 in an assembled condition.
Figure 11:
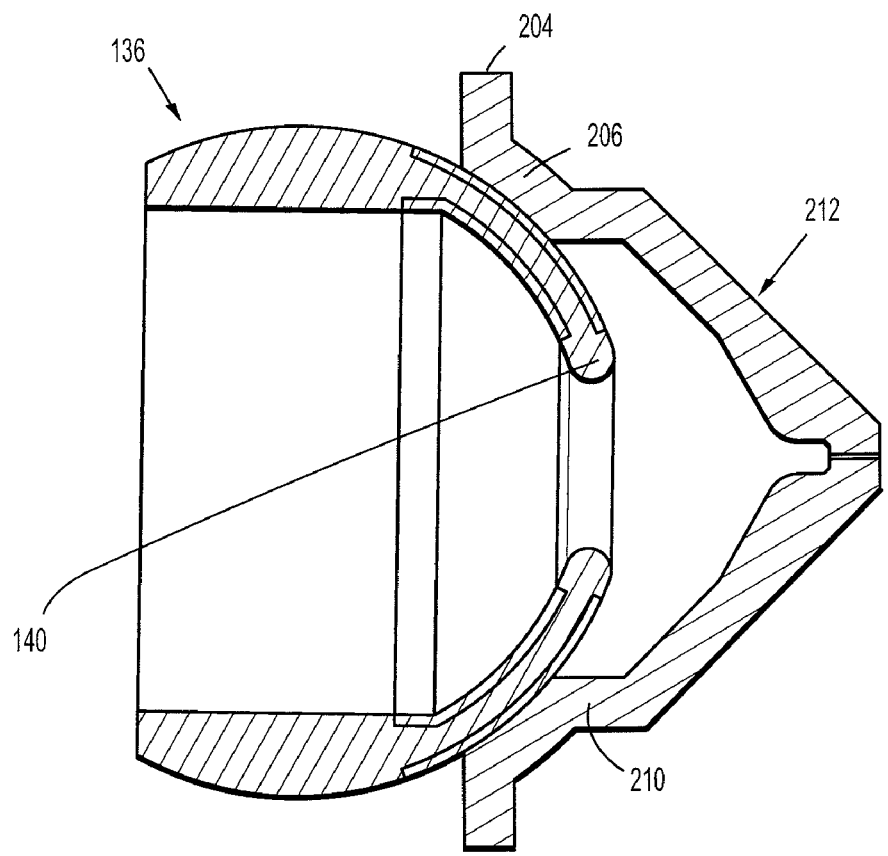
FIG. 11 is a cross-sectional view of the object seal mount and closure valve taken along the lines 11-11 of FIG. 10.

FIGS. 8-9 illustrate a closure valve 200 in accordance with another embodiment of the present disclosure. FIGS. 10-11 illustrate object seal mount 136 in interfacing relationship with closure valve 200. Since object seal mount 136 has been described previously, for simplicity, only closure valve 200 is described in detail herein. Further, those skilled in the art will recognize that, and how, closure valve 200 can be incorporated into access housing 102, in particular, incorporated into first housing segment 106 and into second housing segment 108, with minor modifications to the second housing segment 108.

Closure valve 200 includes substantially circumferential rim or flange 202 with diametrically opposed flats 204. Circumferential flange 202 and flats 204 may reside in a correspondingly dimensioned recess, e.g., defined in second housing segment 108 to restrain closure valve 200 relative to the second housing segment 108. Extending contiguously from circumferential flange 202 is interface segment 206. Interface segment 206 defines an arcuate or curved interfacing surface 208 with a radius "R" generally corresponding to, and possibly approximating, the outer radius of outer mount surface 144 of object seal mount 136. This arrangement provides a two-fold effect. First, curved or contoured interfacing surface 208 in combination with the corresponding outer mount surface 144 increases the surface area or area of contact between object seal mount 136 and interface segment 206 thus enhancing the sealing capabilities of the components and within longitudinal passageway of access apparatus 100. Second, due to this arrangement, object seal mount 136 extends further within second housing segment 208 thus reducing the height or profile of access housing 102.

Closure valve 200 further includes cylindrical extension segment 210 extending contiguously from interface segment 208 and closure segment 212 depending from the extension segment 210. Closure segment 212 is similar to closure segment 156 of closure valve 138 of the embodiment of FIGS. 1-7. Extension segment 210 increases the effective length of closure valve 200 to accommodate object seal mount 136, which, as a result of the dimensions of interfacing segment 206, extends a greater depth within closure valve 200.

While the invention has been particularly shown, and described with reference to the particular embodiments, it will be understood by those skilled in the art that various modifications and changes in form and detail may be made therein without departing from the scope and spirit of the disclosure. Accordingly, modifications such as those suggested above, but not limited thereto, are to be considered within the scope of the disclosure.

What is claimed is:

1. A surgical access apparatus, which comprises:
   an access housing;
   an access member extending from the access housing, the access member defining a longitudinal axis and proximal and distal ends, the access housing and the access member having a longitudinal passage for passage of a surgical object;
   a seal mount disposed within the access housing and having an object seal for forming a seal about the surgical object; and
   a monolithic closure valve mounted to the access housing and distal of the seal mount, the closure valve including an interface segment and a closure segment extending from the interface segment, the interface segment in direct contacting relation with the seal mount and comprising a generally compliable material adapted to maintain a substantial seal with the seal mount and within the longitudinal passageway during angular movement of the surgical object.

2. A surgical access apparatus, which comprises:
   an access housing;
   an access member extending from the access housing and defining a longitudinal axis, and having proximal and distal ends, the access housing and the access member having a longitudinal passage for passage of a surgical object;
   an object seal mount disposed within the access housing and having an object seal for forming a seal about the surgical object, the object seal mount adapted for at least one of angular movement and rotational movement relative to the longitudinal axis upon manipulation of the surgical object; and a closure valve mounted to the access housing and distal of the object seal mount, the closure valve including an interface segment and a closure segment extending from the interface segment, the interface segment in direct contacting relation with the object seal mount and comprising a generally compliable material adapted to maintain a substantial seal with the object seal mount and within the longitudinal passageway during angular movement of the object seal mount.

3. The surgical access apparatus according to claim 2 wherein the closure segment is adapted to substantially close in the absence of the surgical object.

4. The surgical access apparatus according to claim 3 wherein the closure valve is monolithically formed.

5. The surgical access apparatus according to claim 2 wherein the interface segment defines an aperture for at least partially accommodating the object seal mount.

6. The surgical access apparatus according to claim 5 wherein the interface segment defines a sloped interfacing surface adjacent the aperture, the sloped interfacing surface dimensioned to contact the object seal mount and facilitate angular movement thereof and to maintain the substantial seal between the object seal mount and the closure valve.

7. The surgical access apparatus according to claim 5 wherein the object seal mount is a substantially hemispherical member having a curved outer mount surface and the interface segment defines a curved interfacing surface generally corresponding to the curved outer mount surface of the object seal mount, the curved outer mount surface and the curved interfacing surface cooperating to establish the substantial seal between the object seal mount and the closure valve and to facilitate angular movement of the object seal mount.

8. The surgical access apparatus according to claim 5 wherein the access housing includes an inner wall and an outer wall, the object seal mount at least partially accommodated within an open space defined between the inner and outer walls.

9. The surgical access apparatus according to claim 8 wherein the inner wall includes curved surfaces adjacent the object seal mount, the curved surfaces cooperating with a curved inner surface of the object seal mount during angular movement thereof.

10. The surgical access apparatus according to claim 7 wherein the interface segment is dimensioned to be biased against the object seal mount in response to a pressurized environment present in the longitudinal passageway.

\* \* \* \* \*